(12) United States Patent
Waizenegger et al.

(10) Patent No.: US 9,265,544 B2
(45) Date of Patent: Feb. 23, 2016

(54) STERNAL PLATE TYPE STERNAL CLOSURE COMPRISING AN INTEGRAL SEVERING SITE MEMBER

(71) Applicant: Karl Leibinger Medizintechnik GmbH & Co. KG, Mühlheim a.d. Donau (DE)

(72) Inventors: Axel Waizenegger, Muehlheim (DE); Thomas Koett, Kolbingen (DE)

(73) Assignee: Karl Leibinger Medizintechnik GmbH & Co. KG, Muehlheim a.d. Donau (DE)

( * ) Notice: Subject to any disclaimer, the term of this patent is extended or adjusted under 35 U.S.C. 154(b) by 128 days.

(21) Appl. No.: 14/029,430

(22) Filed: Sep. 17, 2013

(65) Prior Publication Data
US 2014/0081337 A1    Mar. 20, 2014

(30) Foreign Application Priority Data
Sep. 18, 2012    (EP) .................................. 12 184 854

(51) Int. Cl.
*A61B 17/80* (2006.01)
*A61B 19/00* (2006.01)

(52) U.S. Cl.
CPC ........... *A61B 17/8076* (2013.01); *A61B 17/809* (2013.01); *A61B 17/8085* (2013.01); *A61B 2019/307* (2013.01)

(58) Field of Classification Search
CPC .................. A61B 17/8076; A61B 17/8085
See application file for complete search history.

(56) References Cited

U.S. PATENT DOCUMENTS

| | | | |
|---|---|---|---|
| 2,580,821 A * | 1/1952 | Toufick Nicola | 606/282 |
| 2002/0128654 A1 | 9/2002 | Steger et al. | |
| 2005/0065521 A1* | 3/2005 | Steger et al. | 606/69 |
| 2006/0015103 A1 | 1/2006 | Burke | |
| 2007/0038218 A1 | 2/2007 | Grevious | |
| 2011/0125193 A1 | 5/2011 | Grevious | |
| 2013/0018425 A1* | 1/2013 | Seldin et al. | 606/286 |

FOREIGN PATENT DOCUMENTS

| | | |
|---|---|---|
| DE | 87 03 432 | 5/1987 |
| DE | 602 08 880 | 11/2006 |
| DE | 20 2010 012 426 | 11/2010 |
| EP | 1 654 994 | 5/2006 |
| WO | WO 03/061493 | 7/2003 |
| WO | WO 2008/073898 | 6/2008 |
| WO | WO 2012/162733 | 12/2012 |

OTHER PUBLICATIONS

European Search Report dated Feb. 18, 2013 from European Application No. 12184854.3.
European Search Report dated Oct. 15, 2013 from European Application No. 13184978.8.

* cited by examiner

*Primary Examiner* — Andrew Yang
(74) *Attorney, Agent, or Firm* — Beyer Law Group LLP

(57) ABSTRACT

The invention relates to a sternal closure for closing a cleft in a sternum, wherein in each of a first and a second securing area at least one hole is provided for receiving bone screws, the two securing areas being adapted to be screwed on each side of the cleft, wherein a severing site member joining the two securing areas and being integrally connected thereto is provided.

12 Claims, 4 Drawing Sheets

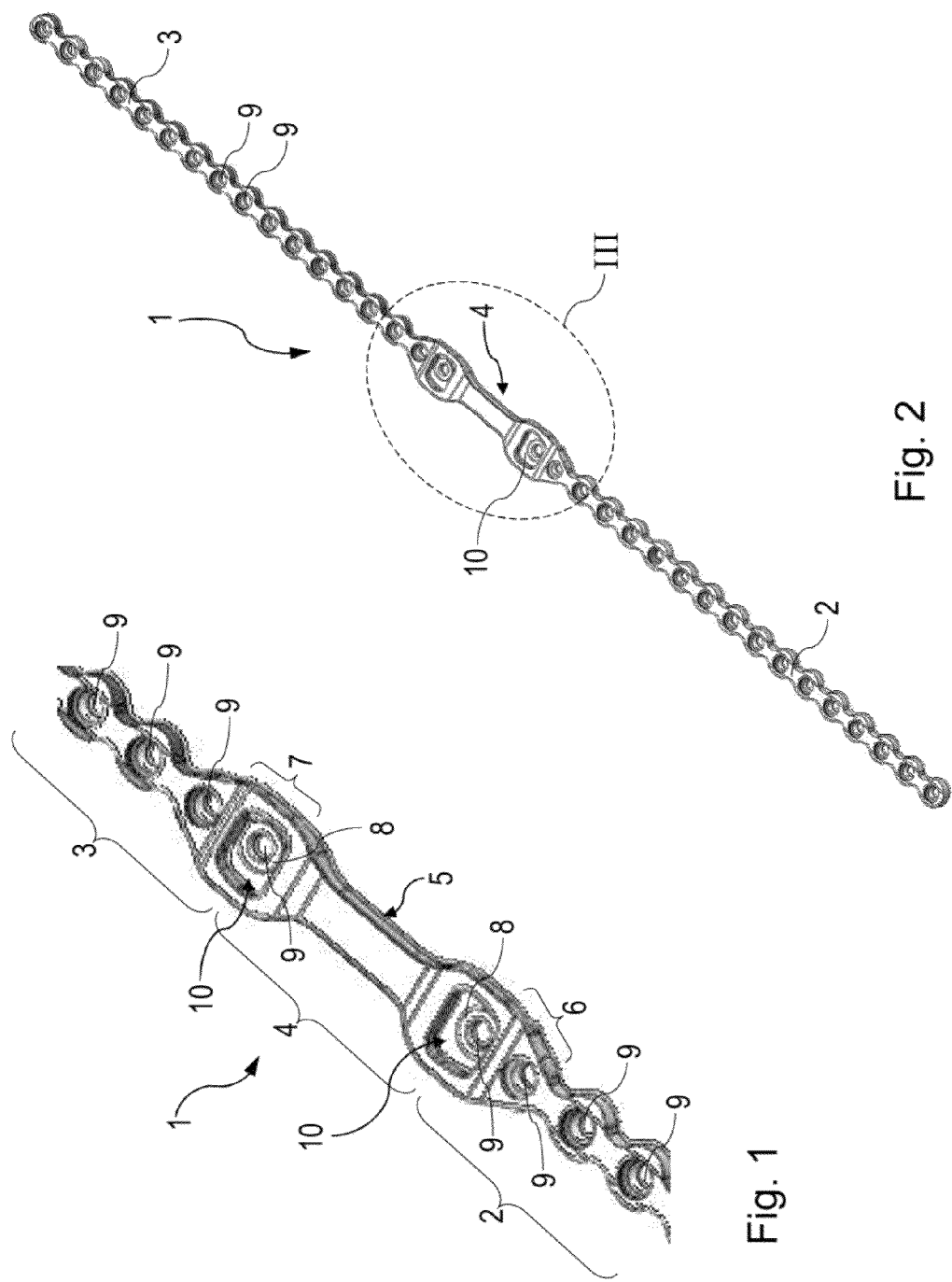

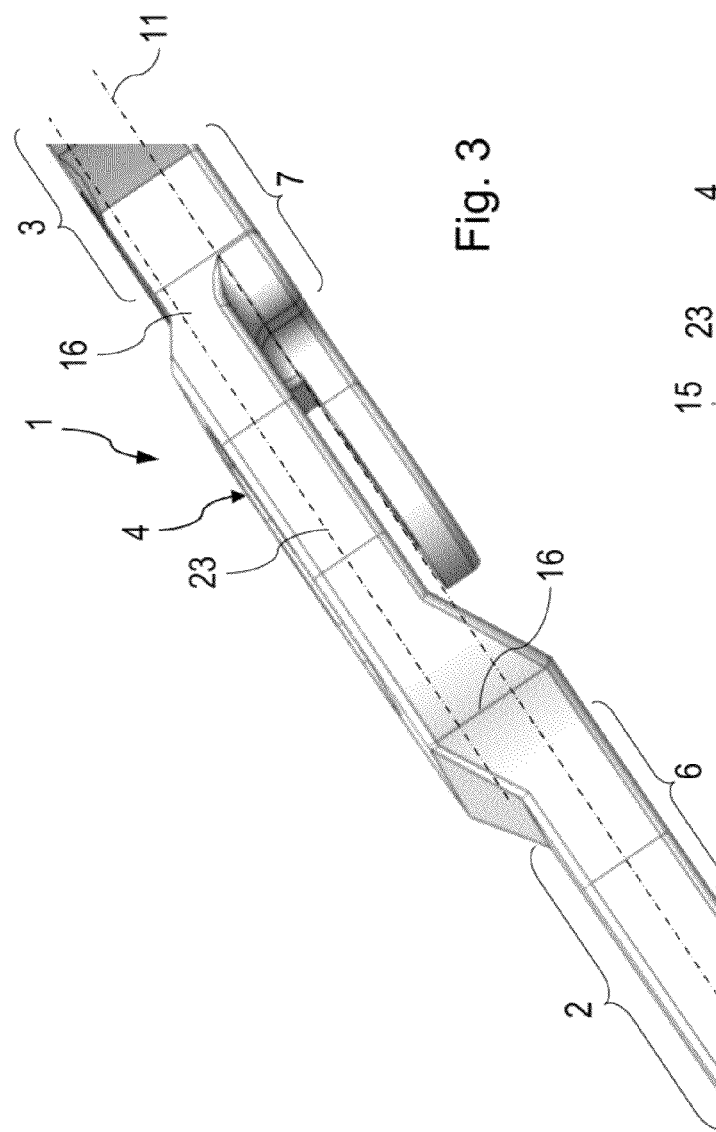
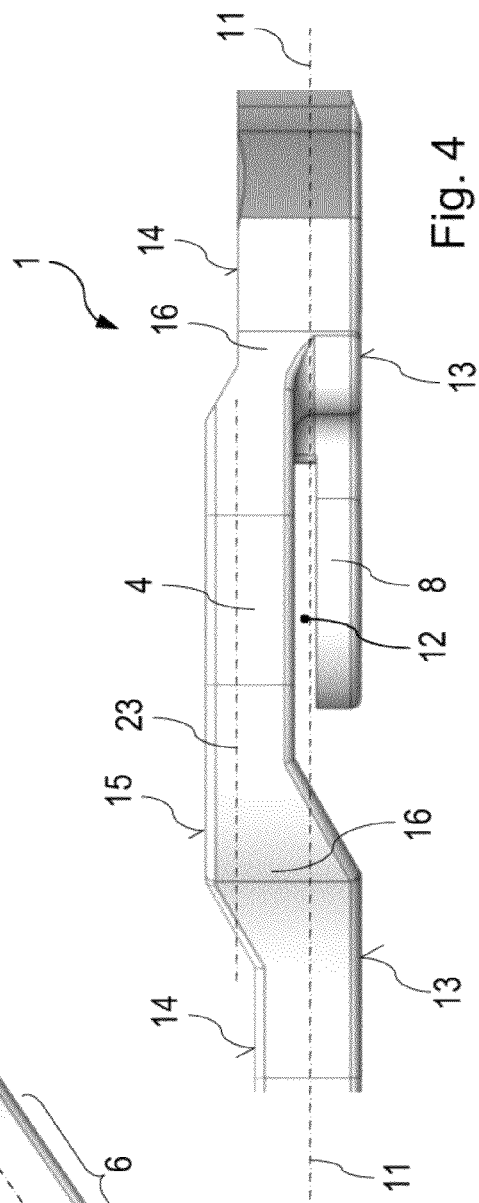

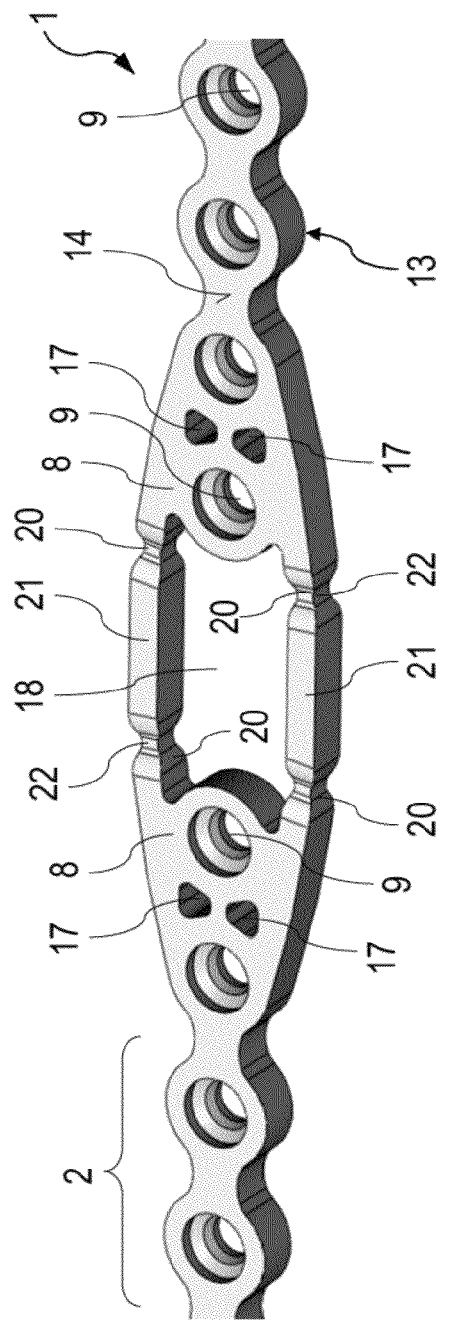
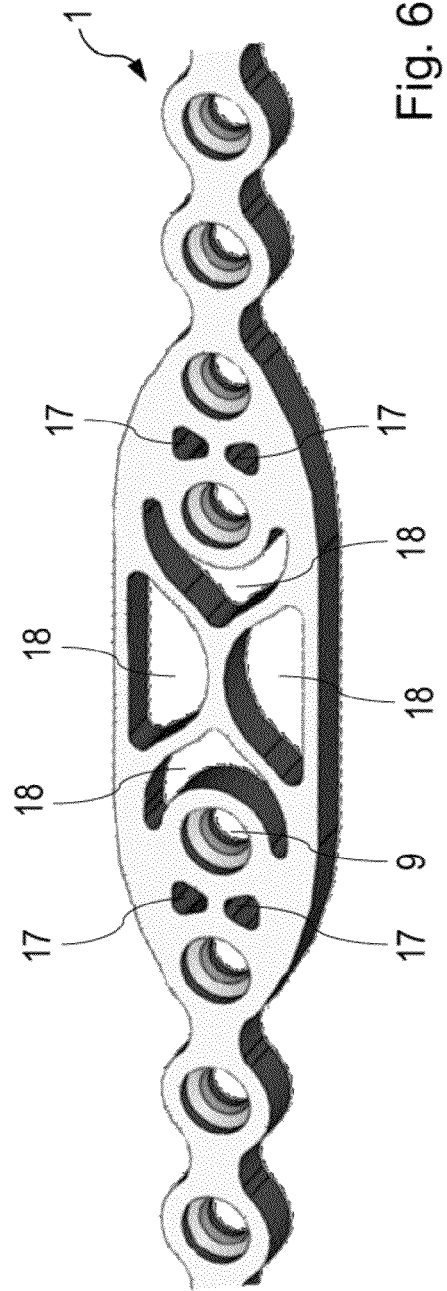

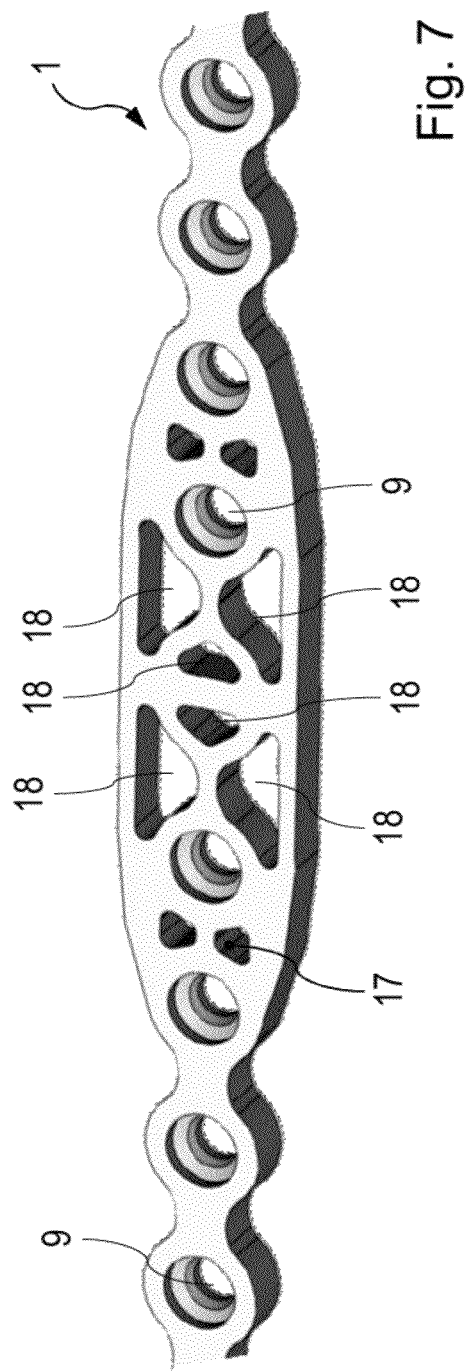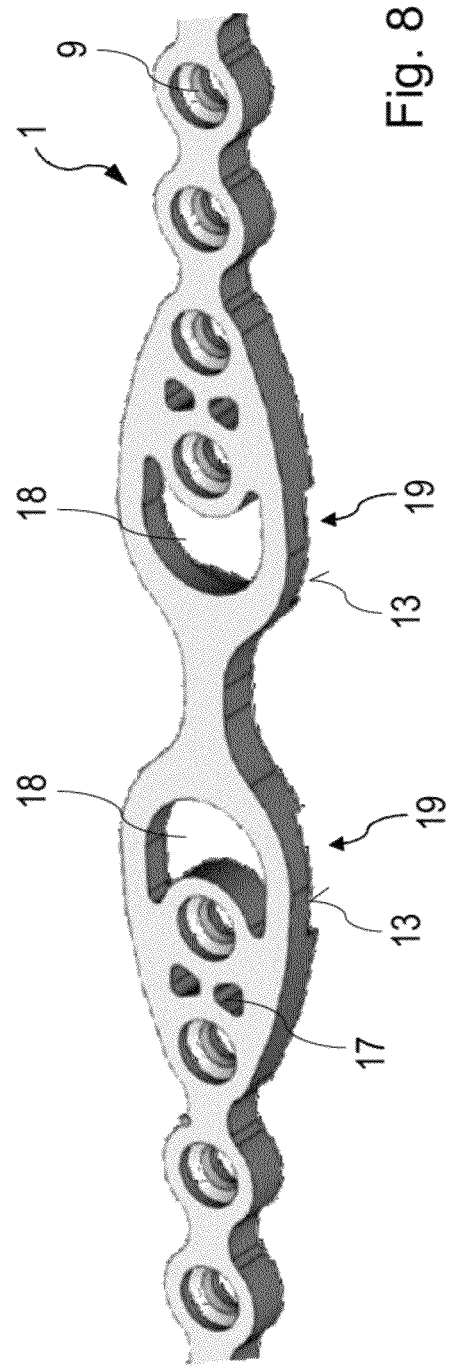

STERNAL PLATE TYPE STERNAL CLOSURE COMPRISING AN INTEGRAL SEVERING SITE MEMBER

CROSS REFERENCE TO RELATED APPLICATIONS

This application claims priority to European Patent Application No. EP 12 184 854.3, filed Sep. 18, 2012, which is hereby incorporated by reference.

FIELD OF THE INVENTION

The invention relates to a sternal closure for closing a cleft in a sternum, wherein in each of a first and a second securing area at least one hole for receiving bone screws is provided, the two securing areas being adapted to be screwed to each side of the cleft by means of the bone screws.

Sternal closures of this type are used for closing a human sternum which was divided before or has a fracture. The bisection of a sternum is necessary especially in the case of operations on the heart. However, the sternum heals relatively slowly, therefore usually a closure means assisting the healing has to be employed.

Conventionally titanium wires have been used, as they are known e.g. from DE 20 2010 012 426 U1.

Sternal closing connections of the cable tie type are also known from DE 87 03 432 U1. There a sternal closing device is disclosed comprising a head member, a flexible backbone member and a tail member, the tail member and the backbone member being adapted to be accommodated in the head member including a locking means on which the backbone member acts such that, when the backbone member is accommodated in the head member, it is prevented from moving backwards, the backbone member further including an upper edge and a lower edge between which a toothing is located, wherein the tail member further includes a sharpened needle formed integrally with the backbone member so as to allow the intercostal tissue to be pierced.

A sternal closure device is also known from US 2007/0038218 A1. There brace members are mounted in the longitudinal direction of the sternum on the same by means of screwed joints, wherein separate connecting elements are secured to the brace members.

Devices for fixing a sternum are also known from DE 602 08 880 P2. The sternum fixing device disclosed there for securing parts of a sternum comprises a first plate having an upper surface and a surface intended for contacting the sternum, wherein a second plate having at least one hook-shaped component for fixation at the sternum and a disengaging component for holding the first and second plates together is used, furthermore the disengaging component being movably connected to at least one of the first and second plates so that it can be moved for separating the two parts of the sternum, wherein especially the first plate includes at least one hole for receiving a disinfectant penetrating the upper surface intended for contacting the sternum.

The known devices exhibit numerous drawbacks, however, which have to be overcome. For example, the variant of titanium wire cuts very strongly into the human tissue so that complications cannot be excluded.

The latter device is very complex and cost-intensive, which results in the fact that those devices are used only in exceptional cases.

The solution making use of the two rods via a separate connecting member, too, is very complex in terms of assembly and has to be improved in this respect.

DISCLOSURE OF THE INVENTION

A generic sternal closure is improved in that a severing site member joining the two securing areas and being integrally connected thereto is provided. Such severing site member or component or severing member or component is removable from the securing areas when the sternal closure is severed.

The following is mentioned for the purpose of delimitation: While a predetermined breaking point is a structural element provided by structural or mechanical and/or physical measures or designs and in the case of damage or excessive load this element will fail in a specific and predictable manner so as to minimize possible damage in an overall system or to achieve a particular function, in the case of the included sternal joint no failure and thus no fracture at a "predetermined breaking point" is intended to occur even in the case of load exceeding the normal extent. The use of a notch or scratch is not necessary though possible. A weakening effect on the component by the notch effect can be avoided.

Advantageously a predetermined breaking point is avoided and rather at a defined site prepared for active severing, for example by means of a tool, it is possible to detach the severing component. Then the severing component acts like a centrally arranged detaching member/component. At the defined site the plate-shaped severing component can be separated from the remainder or an element can be detached.

This detaching member has the greatest additional benefit. By detaching the "central member", i.e. the severing member or severing site component, a relatively wide access to the sternum is open which can be bisected again in the operation theater without removing any screws. The severing site member is arranged to be central, approximately central to the sternum, and adapted to a "midline sternotomy".

The assembly, i.e. surgical integration of the sternal closure then becomes easily possible, wherein even during an emergency operation it is possible to rapidly bisect the sternum so as to immediately reach the organs located below the sternum without complications. In other words, in this case a joining plate is used for a sternal closure, the plate having bores on both sides which can be equipped with screws so as to fix the sternum and the ribs, respectively.

Advantageous embodiments are claimed in the subclaims and will be illustrated hereinafter in detail.

It is beneficial when the severing site member includes a weakened diametric region which also acts can be referred to as severing region. In other words, the severing site member thus includes a severing site, ergo a site which is prepared for intended severing. At such site it is possible to quickly bisect the sternal closure even in critical situations such as an emergency operation. No complicated procedures, such as the removal of screws, have to be gone through. The weakened diametric region can also be provided in that the material in this region offers especially little fracture resistance. In this case it is of advantage when the structure is appropriately acted on. It is also possible to prepare plural regions in accordance with this definition, especially two or four sites.

When the two securing areas are located within a joint first plane at least in the end portions facing each other, the attachment to the ribs and/or the sternum can be managed especially easily.

In order to ensure efficient operation it is of advantage when the severing site member is provided in a second plane spaced apart from the first plane and preferably extending in parallel thereto. An advantageous embodiment is also characterized in that the severing site member is provided on the side of the first plane which is distant from the sternum. While thus a lower side of the securing area or the lower side of both securing areas is provided for contacting the sternum, the severing site member is configured to be spaced apart from the lower side so as to be prepared for a bisecting action of a tool, such as forceps. This allows an especially rapid bisection of the sternal closure.

It has turned out to be especially advantageous in terms of load capacity when one of the two securing areas includes an extension portion provided between the sternum and the severing site member, the extension portion being preferably spaced apart from the severing site member but being adapted to be brought into contact with the sternum. When the thickness of the extension portion is 0.4 to 0.7 times, especially advantageously 0.5 times the thickness of the severing site member, apart from cost-related benefits also benefits in terms of stability are reached. It is of particular advantage when the extension portion has a thickness (measured toward the sternum) of 0.9 mm and the severing site member has a thickness of 1.9 mm. If the distance between the extension portion and the severing site member is 0.5 to 0.9 times the thickness of the extension portion and/or 0.2 to 0.5 times the thickness of the severing site member, especially thin but loadable sternal closures can be configured.

It is furthermore beneficial when in the extension portion a hole for a bone screw is provided. Then the precise positioning of the individual portions is possible.

Also, it is expedient when in each of the two oblong securing portions aligned to each other a plurality of evenly distributed holes is provided. The securing portions then can be secured along one rib or two ribs, respectively, wherein sufficient strength can be produced. In order to ensure the severability during an emergency operation especially well, it is of advantage when the severing site member has a maximum width that is larger than the width of the securing areas. The operating surgeon thus first reaches the severing site member with his/her tool, such as the forceps, and can easily sever the same.

If the severing site member includes at least one cavity or a plurality of cavities, the sternal closure can be configured to be especially light-weight and material-efficient. The severability is not restricted, either.

It has also turned out to be especially efficient when the severing site member includes two rods preferably defining the maximum width of the severing site member.

In this context it is expedient when one rod or each rod is connected to one securing area or both securing areas via one or two thinning sites. It is exactly the thinning sites or sites at which then the sternal closure can be efficiently severed.

The severing site member has turned out to be especially loadable when it exhibits a trussed structure or a dumb-bell shaped or double fork-like structure.

Also, it is expedient when the severing site and/or the thinnings is/are provided in an off-center region of the severing site member.

An advantageous embodiment is also characterized in that the sternal closure is made of a metal alloy such as a titanium alloy and/or plastic material.

Furthermore it is of advantage when the severing site member is arranged centrally above a center line of the sternum, wherein the bisection of the sternum is performed or provided in the area of such center line.

Also for a rapid emergency removal of the severing site member it is useful when a detachability of the severing site member is allowed via non-positive and/or positive and/or adhesive connection types, for example by means of screws and/or pins and/or journals, of further preference without using e.g. a cutting tool.

In this way a plate is provided having at a minimum of two sites a cross-section which is thinned so that easy severing is possible and the access of a "cutter" is optimized. The site at which severing is to be performed can equally be designed to be upwardly offset so that no resting on the bone does occur. Severing of the plate is not performed centrally but off-centered. This ensures that a central piece can be removed and again a "midline sternotomy" can be carried out. In the case of central severing this is possible only with difficulties. Equally in the case of an emergency operation no screws have to be exposed and removed. For the operating surgeon this is beneficial in terms of time saving and for the patient it means the chance that the sternum can be rejoined after bisecting by "standard solutions".

Furthermore it is of advantage when an additional plate and/or an additional member is provided and is inserted in the sternal closure so that the ends of the sternal closure freed from the severing site member are bridged in a non-positive and/or positive and/or adhesive manner (when the emergency operation in an individual's body is completed) and in this case the ends are interconnected by means of the severing site member (prepared for load transmission).

BRIEF DESCRIPTION OF THE FIGURES

Hereinafter the invention will be described in detail also with the aid of a drawing in which different embodiments are shown in which:

FIG. 1 shows a first embodiment of a sternal closure according to the invention in a perspective view.

FIG. 2 shows a view of the sternal closure of FIG. 1 in its entire extension in a representation similar to FIG. 1.

FIG. 3 shows a detailed view of the region III of FIG. 2.

FIG. 4 shows a representation of the cut-out III of FIG. 2 in a representation rotated with respect to FIG. 3.

FIG. 5 is a cut-out of a second variant of a sternal closure.

FIG. 6 is a cut-out of a third variant of a sternal closure.

FIG. 7 is a cut-out of a fourth variant of a sternal closure.

FIG. 8 is a cut-out of a fifth variant of a sternal closure.

The figures are merely schematic and only serve for the comprehension of the invention. Like elements are provided with the same reference numerals.

DETAILED DESCRIPTION

FIG. 1 illustrates a first embodiment of the sternal closure 1 according to the invention. The sternal closure 1 is shown in a central section only. The sternal closure 1 is made of plastic material and/or metal, especially a metal alloy, in the present case of a titanium alloy. In particular the use of high-temperature resistant thermoplastics such as polyetheretherketone (PEEK) or the derivatives thereof, solely or in combination with other materials is imaginable. In this context the biocompatibility has to be taken into account.

The sternal closure is a one-piece component having a first securing area 2 and a second securing area 3. The two securing areas 2 and 3 are interconnected via a severing site member or removing member 4. The severing site member 4 includes a weakened diametric region 5. There the cross-section is smaller than in the surrounding material.

Each of the two securing areas 2 and 3 includes an extension portion 8 at the end zones 6 and 7 thereof facing each other.

The extension portion 8 is covered at least partly by the severing site member 4, wherein above the extension portion recesses 10 of the window type are provided so as to ensure accessibility to a hole 9 in the extension portion. While a hole 9 is provided in each extension portion 8, further holes 9 are also present in the residual securing areas 2 and 3. The holes 9 are configured to receive bone screws not shown, wherein they have an upper larger diametric region and a lower smaller diametric region for retaining a screw head of the bone screws. The bone screws are used to secure the two securing areas 2 and 3 to ribs or to the sternum of a patient, viz. of an individual. The bone screw can also be inserted in the hole 9 of the respective extension portion 8 via the window-shaped recess 10.

During securing the first securing area 2 is secured on the one side of a cleft in the patient's sternum, whereas the second securing area 3 is arranged on the other side of the cleft. As can be clearly perceived in FIG. 2, the holes 9 are equidistant from each other. The sternal closure 1 has an elongate configuration, the two securing areas 2 and 3 being flexible to a certain degree so as to follow a multi-dimensional curve shape. This is advantageous for efficiently ensuring an attachment to the ribs. The individual portions of the sternal closure 1 thus can be adapted to the contour of the patient's bones and cartilage pieces in a joint-like manner.

From FIGS. 3 and 4 it can also be taken that the first securing area 2 and the second securing area 3 are provided in the same first plane 11, at least in the vicinity of the end zones 6 and 7 thereof.

Between the extension portion 8 and the severing site member 4 there is provided a clearance 12, i.e. an empty space or gap. While the lower sides 13 of the two securing areas 2 and 3 as well as of the extension portion 8 are provided at the same level, the surface 15 of the severing site member 4 is positioned above an upper side 14 of the two securing areas 2 and 3. The severing site member 4 is converted into the two securing areas 2 and 3 via a kink 16.

Also, with respect to the FIGS. 3 and 4, it is once more referred to the fact that a second plane 23 is upwardly offset distant from a sternum, wherein the second plane 23 extends through the severing site member 4, whereas the first plane 11 extends through the two securing areas 2 and 3.

In FIGS. 5 to 8 four further embodiments of a sternal closure according to the invention are shown. In these embodiments a recess is provided or better, as presently shown, on each side two recesses 17 are provided which extend completely through the material of the sternal closure from an upper side 14 to the lower side 13.

In the severing site member 4 a cavity 18 is provided which can also be subdivided several times as is shown in the embodiments of FIGS. 6 and 8. As is evident especially in the embodiments of FIGS. 6 and 7, the severing site member can have a trussed structure or, as can especially be taken from FIG. 8, a dumb-bell shaped or double fork-like structure. The individual parts of the trussed structure can have a curved shape.

A double fork-like architecture of the severing site member as illustrated in FIG. 8 can include areas of less material, i.e. areas of reduced thickness, also at the transition areas 19 to the securing areas 2 and 3. Said areas of reduced thickness can be provided on one side of the sternal closure 1, on both sides or alternately on a front and a rear fork side. The thinning is formed on the lower side 13 in this case.

Referring to FIG. 5, it is further noted that the weakened diametric region can also be shaped in the way of thinned sites 20. In this case notches 22 extend around a corresponding rod 21.

The invention claimed is:

1. A sternal closure for closing a cleft in a sternum, comprising:
    a first securing area and a second securing area; and
    a severing site member joining the first and second securing areas and being integrally joined to the first and second securing areas, wherein in each of the first and the second securing areas at least one hole for receiving bone screws is provided, the first and second securing areas being adapted to be screwed on a respective side of the cleft, wherein either of the first and second securing areas includes an extension portion that is at least partially covered by the severing site member and the extension portion is spaced apart from the severing site member, wherein the first and second securing areas are located in a joint first plane at least in end zones facing each other and wherein the severing site member is provided in a second plane which is spaced from the first plane.

2. The sternal closure according to claim 1, wherein the severing site member includes a weakened diametric region.

3. The sternal closure according to claim 1, wherein the severing site member preferably extends in parallel to the first plane.

4. The sternal closure according to claim 1, wherein in the extension portion a hole for a bone screw is provided.

5. The sternal closure according to claim 1, wherein in each of the first and second securing areas a plurality of evenly distributed holes is provided.

6. The sternal closure according to claim 1, wherein the severing site member has a maximum width which is larger than the width of the securing areas.

7. The sternal closure according to claim 1, wherein the severing site member includes at least one cavity or a plurality of cavities.

8. The sternal closure according to claim 1, wherein the severing site member includes two rods preferably defining the maximum width of the severing site member.

9. The sternal closure according to claim 8, wherein one rod or each rod is connected to one securing area or both securing areas via one or two thinning sites.

10. The sternal closure according to claim 1, wherein the severing site member has a trussed structure or a dumb-bell shaped or double fork-like structure.

11. The sternal closure according to claim 8, wherein the severing site and/or the thinning site is provided in an off-center area of the severing site member.

12. The sternal closure according to claim 1, wherein the sternal closure is made of a metal alloy such as a titanium alloy.

* * * * *